United States Patent [19]

Solomon

[11] 4,087,468
[45] May 2, 1978

[54] PREPARATION OF GRIGNARD REAGENTS OF HALODIENES AND PREPARATION OF DIENOLS

[75] Inventor: Paul W. Solomon, Bartlesville, Okla.

[73] Assignees: Phillips Petroleum Company, Bartlesville, Okla.

[21] Appl. No.: 640,296

[22] Filed: Dec. 12, 1975

[51] Int. Cl.$^2$ .................. C07C 29/00; C07F 3/02; C07C 29/00; C07F 3/02

[52] U.S. Cl. .................. 568/807; 260/665 G; 568/809; 568/813; 568/816; 568/828; 568/838; 568/839; 568/878

[58] Field of Search .......... 260/638 G, 665 G, 617 R, 260/618 R

[56] References Cited

U.S. PATENT DOCUMENTS

| | | | |
|---|---|---|---|
| 2,464,751 | 3/1949 | Richter | 260/665 G |
| 2,552,676 | 5/1951 | Hill | 260/665 G |
| 2,813,886 | 11/1957 | Ramsden | 260/665 G |
| 2,872,471 | 2/1959 | Ramsden et al. | 260/665 G |
| 3,041,320 | 6/1962 | Chanin et al. | 260/82.1 |
| 3,083,242 | 3/1963 | Ramsden | 260/665 G |
| 3,168,582 | 2/1965 | Aufdermarsh | 260/665 G |
| 3,418,304 | 12/1968 | Langer et al. | 260/665 G |
| 3,706,809 | 12/1972 | Moroe et al. | 260/638 G |
| 3,758,620 | 9/1973 | Vit | 260/665 G |

FOREIGN PATENT DOCUMENTS

| | | | |
|---|---|---|---|
| 708,995 | 5/1965 | Canada | 260/665 G |
| 280,476 | 11/1970 | U.S.S.R. | 260/665 G |

OTHER PUBLICATIONS

Kharasch, et al., "Grignard Reactions of Nonmetallic Substances," (1954), p. 11.
Ramsden, et al., "J. Org. Chem.", vol. 22, (1957), pp. 1602–1605.

Primary Examiner—Joseph E. Evans

[57] ABSTRACT

Grignard reagents of halo-substituted conjugated dienes are prepared by reaction of 1- or 2-halo-substituted conjugated diene with magnesium metal employing a metal halide/saturated aliphatic halide catalyst system. The Grignard reagent can be employed in the preparation of hydroxy-substituted conjugated dienes and hydroxy-substituted allenes. Adjustment of the molar ratio of the metal halide to the halo-substituted conjugated diene permits favoring of hydroxy-substituted conjugated dienes or hydroxy-substituted allenes in the diene products.

38 Claims, No Drawings

PREPARATION OF GRIGNARD REAGENTS OF HALODIENES AND PREPARATION OF DIENOLS

FIELD OF THE INVENTION

The invention relates to the preparation of Grignard reagents. In another aspect, the invention relates to the preparation of hydroxy-substituted conjugated dienes and hydroxy-substituted allenes.

BACKGROUND OF THE INVENTION

Dienol compounds, such as hydroxy-substituted conjugated dienes, are useful comonomers in polymerization with other conjugated dienes, such as butadiene, or in the copolymerization of conjugated dienes with monovinyl-substituted aromatic compounds, so as to produce elastomeric compositions containing a high functionality, i.e., a relatively large number of hydroxy groups per molecule. Highly functional polymers are desirable in the preparation of castable rubbers, by which a liquid or semisolid feedstock can be fully cured by heat/pressure treatment to form a highly resilient rubbery product. The highly functional elastomers have improved properties and exhibit greater utility in that they can be easily cured by means other than conventional sulfur vulcanization. Allenic hydroxy-substituted dienes are useful intermediates for a variety of purposes.

The allenic dienols can be used as drying oils in paints, or can be used in other chemical processes. The allenic dienes can be readily converted to hydroxy-substituted acetylenics. Addition of amines to the double bonds results in corrosion inhibitors. Addition of halogens to the double bonds results in useful solvents with both polar and non-polar segments.

Unfortunately, use of such dienol compounds has been very limited since extant methods of preparation have been complex and costly.

BRIEF SUMMARY OF THE INVENTION

I have discovered a simple, straightforward, effective method for the preparation of hydroxy-substituted conjugated dienes and hydroxy-substituted allenes by a synthesis involving Grignard reagents of halo-substituted conjugated dienes. In another aspect, I have discovered a method by which these formerly very difficult to prepare Grignard reagents can be simply prepared. In a still further aspect, I have discovered a method of favoring the ultimate dienol product distribution between the hydroxy-substituted conjugated dienes and the hydroxy-substituted allenes.

The novel Grignard reagents of halo-substituted conjugated dienes are prepared by contacting magnesium metal together with a saturated aliphatic halide, a metal halide of zinc, cadmium, indium or mercury, and a 1- or 2-halo-1,3 conjugated diene in a suitable ether solvent.

The resulting Grignard reaction products can be reacted with carbonyl compounds, aldehydes or ketones, to produce addition products, which then are hydrolyzed to produce the desired hydroxy-substituted conjugated dienes and hydroxy-substituted allenes which are referred to herein collectively as dienols.

When conjugated dienols are desired, it is presently preferred to employ in the Grignard preparation a molar ratio of metal halide:halo-diene of at least about 0.2:1, preferably about 0.2:1 to 0.8:1; and presently most preferred to use the 2-halo-1,3-dienes. However, when the allenic dienols are desired, then it is presently preferred to use a molar ratio of metal halide:halo-diene of less than about 0.2:1, preferably about 0.005:1 to 0.1:1. Thus in accordance with this aspect of my invention, I can control or favor the preponderance of conjugated or allenic product in the dienol mixture obtained.

It is readily apparent that the Grignard reagents, as prepared by our process employing the novel catalyst and cocatalyst system, are not simple Grignard species as might be conventionally represented, but rather are novel complex and unusual species. While we cannot at this time be certain of their chemical character, and do not wish to be bound by theorizations on possible structures, the unique and unusual character of our Grignard species is clearly demonstrated by their unexpected abilities in the formation of either conjugated or allenic, or vice versa, hydroxy-dienes (dienols).

DETAILED DESCRIPTION OF THE INVENTION

Halo-Substituted Dienes

The halo-substituted dienes employed are the 1-halo or 2-halo-1,3-hydrocarbyl dienes. In these 1- or 2-halo-1,3 dienes, the halogen can be chlorine, bromine or iodine. Presently preferred are the chlorine substituted compounds because of their ready availability and relatively low cost.

These 1- or 2-halo-1,3-dienes also can be represented by the isomeric formulae:

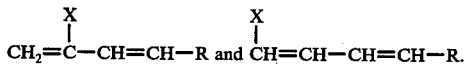

In each formula, X is chlorine, bromine or iodine. R represents either hydrogen, or a lower alkyl radical. Preferably R is hydrogen or an alkyl radical of 1 to 4 carbon atoms, and presently most preferred are the species in which R is hydrogen, particularly further preferred is the 2-halo species where X is chlorine and the species is 2-chloro-1,3-butadiene.

Other exemplary species include such as 2-bromo-1,3-butadiene, 2-iodo-1,3-butadiene, 1-bromo-1,3-butadiene, 1-chloro-1,3-butadiene, 1-iodo-1,3-butadiene, 2-chloro-1,3-pentadiene, 2-bromo-1,3-heptadiene, 2-iodo-1,3-octadiene, and the like, as well as mixtures where desired or where commercially necessary depending on the raw material sources. The process of my invention appears particularly suitable for the conversion of the 2-halo-1,3-hydrocarbon dienes, presently preferred being 2-chloro-1,3-butadiene, because of its commercial availability.

MAGNESIUM METAL

The magnesium metal employed should be of a quality suitable for Grignard-type reactions. It is preferably employed as a finely divided solid in the form of coarse powders, turnings, and the like. The magnesium metal should be of high purity substantially free of oxidized material so that the metal surface is available for reaction.

METAL HALIDES

The metal halides employed in the formation of the Grignard reagents comprise the zinc, cadmium, mercury, and indium metal halides, wherein the halide is the chloride, bromide, or iodide. These metal halides also can be represented by the formula $MX_a$ wherein X is the aforesaid halide; M is the metal selected from those mentioned; and $a$ is the valence of M, having a value of 2 with zinc, cadmium, or mercury, and a value of 3 in the case of indium. Presently preferred are the zinc halides, most particularly zinc chloride, because of its relatively low cost and ready availablity, as well as its high degree of effectiveness exhibited in runs disclosed hereinafter.

SATURATED ALIPHATIC HALIDES

The saturated aliphatic halides are the bromides, chlorides, and iodides, with the proviso that the saturated aliphatic chlorides further require the presence of elemental iodine as a copromoter in a minor effective amount. In the case of the saturated aliphatic bromides and iodides iodine optionally further can be employed and is not objectionable, but presently appears unnecessary. These saturated aliphatic chlorides, bromides, and iodides are of the lower alkyl or alkylene type, and presently preferably contain 1 to 4 carbon atoms per molecule because of availability and cost.

These saturated aliphatic halides can be represented by the general formula $R'X_b$. In this formula, $R'$ is a lower alkyl or alkylene radical with a valence of $b$; X is the halide as before defined; and $b$ corresponds to the number of halogen atoms per molecule, and can be 1 or 2.

Exemplary species include such as methyl chloride, methyl iodide, 1,2-dichloroethane, ethyl chloride, isopropyl chloride, n-propyl chloride, methyl bromide, ethyl iodide, tert-butyl chloride, sec-butyl chloride, isobutyl chloride, n-butyl chloride, 2,2-dichloropropane, 1-bromo-1-chloroethane, the corresponding bromides, the corresponding iodides, and the like, including mixtures; where elemental iodine also is required, mixtures such as a minor amount of iodine with isopropyl chloride or n-propyl chloride can be employed.

ETHER DILUENT

Ether diluents employed are selected from the group consisting of tetrahydrofuran, 1,4-dioxane, dimethyl ether of ethylene glycol, dimethyl ether of diethylene glycol, diethyl ether of ethylene glycol, diethyl ether of diethylene glycol, alone, or in admixture, and optionally with a hydrocarbon.

The ether diluent preferably is employed alone. However, minor amounts of a hydrocarbon codiluent, e.g., saturated aliphatic hydrocarbons such as hexane, octane, or higher liquid hydrocarbon, or liquid aromatic hydrocarbons such as benzene, and the xylenes, can be employed. Chloroprene, for example, can be obtained commercially as a concentrated solution in xylene which can be used directly without deleterious effects and without removal of the xylene solvent from the chloroprene, unless the material contains an antioxidant in which case separation of the xylene-chloroprene admixture from the antioxidant becomes necessary.

CARBONYL COMPOUNDS

The carbonyl compounds employed in the process of one aspect of my invention, wherein the Grignard reagent of the 1- or 2-halo-1,3-diene is further converted to a dienol, are the aldehydes and ketones.

The aldehydes and ketones, respectively, can be represented by $R''CHO$ and $R''COR'''$, wherein $R''$ is either hydrogen, or an alkyl, aryl, cycloalkyl, or combination radical. Because of availability aldehydes containing 1 to 12 carbon atoms per molecule are preferred. $R'''$ is an alkyl, cycloalkyl, aryl, or combination hydrocarbon radical, such that the ketone preferably contains 3 to 15 carbon atoms per molecule. Mixtures of carbonyl compounds can be employed, though much less desirably, resulting in a mixture of end-products.

Exemplary aldehydes and ketones include formaldehyde, acetaldehyde, propionaldehyde, glyoxal, isobutyraldehyde, paraldehyde, benzaldehyde, n-butyraldehyde, phenyl acetaldehyde, cyclohexyl acetaldehyde, n-decanal, any of the tolualdehydes, and the like. Formaldehyde has been found particularly useful in the process of the invention and is readily available at low cost.

Among exemplary ketones are acetone, ethyl methyl ketone, isopropyl-methyl ketone, acetophenone (phenyl methyl ketone), methyl cyclohexyl ketone, benzophenone (diphenyl ketone), and the like.

DIENOLS

The dienols produced by one aspect of my invention can be represented by the formulae:

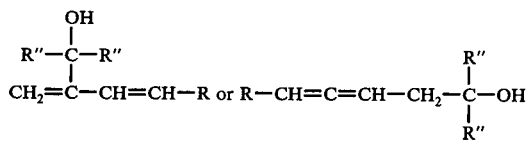

wherein each R and $R''$ is as previously defined. When formaldehyde is employed in the reaction process, the product is a primary alcohol. When higher aldehydes are used, the products are secondary alcohols. When ketones are used, the products are tertiary alcohols.

Reactions wherein the two aforementioned types of halodienes are employed initially yield a mixture of two dienols, though the ratio of the two dienol products one with the other can be varied as desired, depending on operational conditions and catalyst concentrations, and furthermore the conjugated dienol can be made to substantially predominate over the allenic isomer, where desired, by employing relatively large amounts of metal salt catalysts. Reactions wherein the 1-halo-1,3-dienes are employed initially generally give better yields of the corresponding conjugated dienols preferably with relatively large amounts of metal salt catalysts.

REACTION CONDITIONS

In the preparation of the Grignard reagent in accordance with the process of my invention, the 1-halo or 2-halo-1,3-hydrocarbyl diene is contacted as a solution in the ether or ether/hydrocarbon diluent with the magnesium metal in the further presence of the metal halide catalyst and the saturated aliphatic halide promoter, and iodine as desired or necessary. The resulting product is a novel Grignard intermediate, termed a Grignard reagent.

The Grignard forming conditions can vary widely. Exemplary temperatures employed lie in the range of about 10° C. to about 100° C.; employing any pressure convenient or suitable to maintain the reactants and diluent substantially in the liquid phase. The overall reaction can be conducted in any convenient total amount of ether or ether/hydrocarbon diluent which will suitably disperse and dissolve the reactants to minimize the formation of any locally high concentration of starting materials and product, thus minimizing or avoiding any potentially undesirable side reactions such as coupling. The total amount of diluent employed in the overall reaction system exemplarily can be in the range of about 1 to 100 times the weight of the 1- or 2-halo-1,3-diene since less than this does not give sufficient dilution and greater than this is simply an excess amount of unnecessary diluent to handle.

The order of addition does not appear critical, and the reactants can be added to the diluent in any convenient order. In practice, a solution of the 1- or 2-halo-1,3-diene in ether or ether/hydrocarbon, can be added slowly to an ether dispersion of the magnesium metal plus the promoter the saturated aliphatic halide plus the metal halide catalyst. The reaction is exothermic and preferably is carried out under reflux conditions so as to remove excess heat as generated. Other sequences of addition can be employed, though this is preferred and is safest in actual practice. The reaction time can vary widely, such as from a few minutes to several hours, such as about 0.5 hour to 24 hours.

The amount of magnesium metal employed in the reaction system in preparation of the Grignard reagent preferably is in at least a slight molar excess of the amount of 1- or 2-halo-1,3-diene to help assure complete reaction with the magnesium metal in a reasonable time. In practice, however, from about 0.8 to 1.5 moles of magnesium metal generally can be employed per mole of the halo-1,3-diene to obtain satisfactory results.

Presently employed is a molar ratio of metal halide catalyst to the 1- or 2-halo-1,3-diene reactant in the range of about 0.005:1 to about 0.8:1, so as to produce the desired Grignard reagent of the 1- and/or 2-halo-1,3-diene.

When 2-halo-1,3-dienes are employed, and particularly ultimately where conjugated dienols are desired as the principal product, the molar ratio of metal halide to the 2-halo-1,3-diene should be above about 0.2:1, preferably in the range of about 0.2:1 to 0.8:1, and presently more preferred being a ratio of about 0.5:1 as having given particularly efficient results in my experience.

If the corresponding allenic isomers are desired as principal ultimate products, then the presently preferred ratio is less than about 0.2:1, preferably about 0.005:1 to 0.1:1. It has been observed in my work that when relatively small amounts of the metal halides are employed in my process that such levels tend to favor the allenic products, while relatively large amounts favor the production of the conjugated product.

When 1-halo-1,3-dienes are to be converted, it appears that results favoring the conjugated dienols are obtained wherein a molar ratio of metal salt to the 1-halo-1,3-diene is above about 0.2:1, preferably in the range of about 0.2:1 to 0.8:1.

When a saturated aliphatic chloride is employed, then a small amount of iodine is added, and this need only be that small amount suitable to effectuate the reaction desired.

The molar ratio of saturated aliphatic halide promoter to metal salt can range widely, so long as the ratio is effective to produce the desired Grignard reagent. An exemplary range is about 0.02:1 to about 50:1, presently preferred about 5:1 to 20:1.

REACTION WITH CARBONYL COMPOUND

The resulting Grignard reagent can be employed, without isolation from the diluent, and without otherwise treating the resulting solution of the Grignard reagent, by contacting the reaction product in the diluent with a carbonyl compound, which is an aldehyde or ketone, to produce an addition product, and thereafter hydrolyzing the product to produce the desired dienol.

In practice, the Grignard reagent is contacted promptly with the carbonyl-containing compound, and this is conveniently accomplished in the original reaction means and diluent. However, it is feasible to transfer the reaction product, the Grignard reagent, from the first step to another reaction means if desired for contact with the carbonyl compound. In handling of all these reagents, and in any such transfer, as well as in contact with the carbonyl-containing compound, because of the sensitivity of Grignard reagents to the presence of moisture, all such reagents, the compounds forming them, catalysts, promoters, and the like, including reaction means, should be essentially free of moisture.

The selected carbonyl compound, or an ether or ether/hydrocarbon solution thereof, can be added to the Grignard reaction product of the first step over a suitable time interval so as to obtain the desired rate of reaction. A suitable reaction time can range widely, such as from a few minutes to several hours, such as from about 0.1 to 5 hours. Ordinarily, the molar ratio of carbonyl compound to halo-1,3-diene originally employed will be in the range of from about 0.8:1 to 2.0:1.

In this aspect of my process, preferably somewhat lower temperatures are employed, though the ranges overlap, such as about $-50°$ C. to $+75°$ C., again under a suitable pressure sufficient to maintain reaction substantially in the liquid phase.

After the carbonyl addition has been completed and the reaction substantially completed, the reaction product at this stage then is hydrolyzed so as to produce the desired hydroxy-substituted conjugated diene, together with isomeric allenic alcohol.

For the hydrolysis step, the reaction mixture can be quenched with water, preferably cold water, and including a mineral acid such as hydrochloric acid, or by adding an ammonium halide such as ammonium chloride, as is well known in the hydrolysis art. Phase separation occurs, and the organic phase can be readily separated, such as by decantation, and/or with the employment of extractive reagents such as ethers. Ethereal extracts can be further purified such as by washing with water and distillation to yield the desired organic dienol product.

In the higher resulting dienols, obtained by starting with such as a chloro-substituted pentadiene, or higher number of carbon atom conjugated diene, the end product obtained, the corresponding dienol, exhibits considerable proportions of cis structure, in contrast to dienol materials obtained by heretofore employed radical or carbonium ion methods which yield substantially trans isomers. The cis isomers frequently are preferred for employment in the preparation of elastomers.

EXAMPLES

Examples presented herein are designed to assist in an understanding of my invention. Exemplary species employed, specific conditions, proportions, and the like, should be considered as exemplary, not as limitative of the scope of my invention.

EXAMPLE I 272 g (2 moles) of zinc chloride were placed in an oven-dried 5-liter 3-necked round bottomed flask fitted with mechanical stirrer, 1-liter dropping funnel, nitrogen inlet tube, and ice-water cooled Friedrick condenser. The zinc chloride was melted under a nitrogen purge to remove all traces of moisture from the metal chloride catalyst. 116 g (4.8 moles) of magnesium turnings and 2 liters of anhydrous tetrahydrofuran (THF) were added to the reaction flask. The mixture was heated to boiling to dissolve the zinc chloride, and 114 g (0.8 mole) methyl iodide were added dropwise to the reaction mixture over a period of 30 minutes. Vigorous boiling and foaming occurred during the methyl iodide addition, though the reaction mixture was readily contained in the reaction system. The reaction mixture at this point was a light gray suspension.

After foaming had stopped, 352 g (4 mole) of 2-chloro-1,3-butadiene (chloroprene) in one liter of anhydrous THF were added dropwise over a period of two hours. During the addition of the first 500 ml of the THF solution, approximately 30 minutes, gentle refluxing and foaming occurred as the reaction mixture became dark tan. At this point boiling became very vigorous and the reaction mixture had to be cooled by external water-bath cooling for about 10 to 15 minutes. After the vigorous reaction had subsided, heating of the reaction mixture was resumed and continued during the addition of the remaining THF solution over approximately 2 hours. The reaction mixture was boiled for an additional two hours after all the THF/2-chloro-1,3-butadiene solution had been added. The reaction mixture at this point was gray-black.

The stirred reaction mixture was cooled to −30° C. and formaldehyde from the pyrolysis of 101 g (3.4 moles) paraformaldehyde was swept by nitrogen into the reaction system over a period of one hour. After all the formaldehyde had been added, the reaction mixture was stirred for an additional 30 minutes at −30° C. The reaction mixture was warmed to 50° C., and then cooled to room temperature before pouring into a mixture of ice and water (approximately 8 liters) containing 1000 g ammonium chloride.

This mixture was extracted twice with 2000 ml portions of ether, and 4 g of phenothiazine inhibitor was added to the combined ether extracts. The ethereal extract was filtered, washed with 500 ml of 5 percent aqueous sodium bicarbonate solution and dried over anhydrous magnesium sulfate before distillation through an 18 inch Vigreux column. Distillation gave 170 g (yield 78 percent) of product (b.p. 42°–43° C./10 mm) of about 96 weight percent isopropenyl alcohol (a conjugated dienol 2-hydroxymethyl-1,3-butadiene) and 3.4 weight percent 3,4-pentadien-1-ol (an allenic alcohol), balance was 0.6 weight percent THF.

This run describes an aspect of my inventive process as a convenient synthetic route to the preparation of isopropenyl alcohol (2-methylene-3-buten-1-ol). It is to be noted that my inventive process as described using the optimal Grignard/ZnCl$_2$ ratio of 2:1 favors the production of the 1,3-dienol, viz., isoprenyl alcohol (2-methylene-3-buten-1-ol) over the production of the coproduct allenic alcohol, viz., 3,4-pentadien-1-ol.

EXAMPLE II

This comparative run describes the reaction of 2-(1,3-butadienyl)-magnesium chloride Grignard reagent, prepared in the absence of a metal halide catalyst, with formaldehyde (see the procedure of R. D. Rieke and S. E. Bales, J. Chem. Soc., Chem. Comm., 1973, 879–880). The major product was 3,4-pentadien-1-ol, an allenic alcohol.

Into a 3-necked 500 ml roundbottomed flask equipped with mechanical stirrer, condenser, nitrogen inlet tube, and dropping funnel were added 200 ml anhydrous tetrahydrofuran (THF) followed by 7.5 g (180 mg-atoms) of freshly cut potassium, 10.2 g (110 mmoles) anhydrous magnesium chloride, and 8 g (50 mmoles) of oven-dried potassium iodide. The stirred mixture was boiled for 2 hours to give a purple-black suspension. After cooling the reaction mixture to 22° C., 4.5 g (50 mmoles) of 2-chloro-1,3-butadiene (chloroprene) in 50 ml anhydrous THF were added. A small temperature rise to 28° C. was noted within 10 minutes, and, on stirring for an additional 60 minutes, the temperature of the reaction mixture returned to about 22° C. The reaction mixture was refluxed for 30 minutes, then cooled to −30° C. and 1.5 g (50 mmoles) of formaldehyde from the pyrolysis of paraformaldehyde were swept by nitrogen into the reaction system.

The reaction mixture was warmed to 50° C. and then cooled to room temperature for work-up. The reaction mixture was poured onto a mixture of 50 g ammonium chloride dissolved in 400 ml of ice/H$_2$O, and extracted three times with 200 ml portions of ether. The ether phases were separated, combined together and filtered through a glass wool plug, and phenothiazine (0.1 weight percent) inhibitor was added to the ethereal filtrate. The ethereal filtrate was washed with 50 ml of 5 percent aqueous sodium bicarbonate, dried over anhydrous magnesium sulfate and distilled to give only a 58 percent yield of C$_5$ dienols of 16 percent 2-methylene-3-buten-1-ol (isoprenyl alcohol) and 42 percent 3,4-pentadien-1-ol (allenic isomer).

EXAMPLE III

A number of compounds were examined as promoters for the metal halide catalyzed 2-halo-1,3-diene reaction with magnesium. When promotion was achieved, the resulting Grignard product was further reacted with an aldehyde, here formaldehyde, ultimately to form the desired dienol.

Each run utilized 200 mmoles of 2-chloro-1,3-butadiene, 4 mmoles methyl iodide, and 240 mmoles of formaldehyde (or in some cases 230 mmoles of benzaldehyde). Results of comparative runs with the zinc chloride are included for comparisons. Runs 3 and 4 employed formaldehyde. Other Runs 5 through 9, inclusive, employed benzaldehyde. Results are shown in table form for convenience.

Table I

Production of 1,3-Dienols and Allenic Alcohols From 2-(1,3-Butadienyl)magnesium Chloride and Carbonyl Compounds in the Presence of Methyl Iodide Promoter and Various Catalytic Salts

| Run No. | Catalyst | Mmoles | Time For Grignard Formation (Hr.) | Total Alcohol Yield | Ratio of 1,3-Dienols to Allenic Alcohols (a) |
|---|---|---|---|---|---|
| 3 | ZnCl$_2$ | 2.3 | 0.5 | 67 | 0.45 |
| 4 | InCl$_3$ | 1.4 | 18 | 50 | 0.58 |
| 5 | ZnCl$_2$ | 2.2 | 1 | 69 | 0.15 |
| 6 | ZnBr$_2$ | 1.3 | 0.5 | 73 | 0.17 |
| 7 | ZnI$_2$ | 1.0 | 2 | 69 | 0.16 |
| 8 | CdCl$_2$ | 2.0 | 8 | 55 | 0.19 |
| 9 | HgCl$_2$ | 2.0 | 21 | 34 | 0.19 |

(a) In the formaldehyde Runs 3 and 4, the 1,3-dienol is isoprenyl alcohol (2-methylene-3-buten-1-ol) and the allenic alcohol is 3,4-pentadien-1-ol. In the benzaldehyde runs 5–9, the 1,3-dienol is represented by structure (C) and the allenic alcohol is represented by structure (D) below:

1-phenyl-2-methylene-3-buten-1-ol

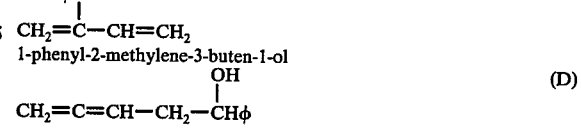

Table I-continued
Production of 1,3-Dienols and Allenic Alcohols From 2-(1,3-Butadienyl)magnesium Chloride and Carbonyl Compounds in the Presence of Methyl Iodide Promoter and Various Catalytic Salts

| Run No. | Catalyst | Mmoles | Time For Grignard Formation (Hr.) | Total Alcohol Yield | Ratio of 1,3-Dienols to Allenic Alcohols (a) |
|---|---|---|---|---|---|
| 1-phenyl-3,4-pentadien-1-ol | | | | | |

These runs show that relatively low ratios of metal salt to the halodiene favor the formation of the allenic alcohol.

EXAMPLE IV

In a manner similar to that of Example I, 2-chloro-1,3-butadiene was converted to the corresponding alcohols by the process of my invention in a series of runs in which the amount of metal salt was varied. In each run, 200 mmoles of the chloroprene was added to a reaction mixture containing 40 mmoles of methyl iodide. The results of these tests are shown in Table II below:

Table II
Production of Isoprenyl Alcohol and 3,4-Pentadien-1-ol From 2-Chloro-1,3-Butadiene and Formaldehyde in the Presence of Zinc Chloride and Methyl Iodide

| Run No. | Molar Ratio $ZnCl_2$/diene | % Selectivity Isoprenyl Alcohol | % Yield (Total) Isoprenyl Alcohol 3,4-Pentadien-1-ol |
|---|---|---|---|
| 10 | 0.012 | 31 | 67 |
| 11 | 0.17 | 48 | 65 |
| 12 | .30 | 76 | 60 |
| 13 | .50 | 96 | 58 |
| 14 | .55$^a$ | 94 | 43 |
| 15 | .75$^a$ | 87 | 26 |
| 16 | 1.0$^a$ | 86 | 24 |

$^a$The Grignard reagent 2-(1,3-butadienyl)magnesium chloride was prepared using a 0.012 $ZnCl_2$/diene ratio first as in Run 10 and then additional $ZnCl_2$ was added. The molar ratio $ZnCl_2$/diene column shows the total number of $ZnCl_2$ millimoles added to the system.

These data illustrate that the reaction can be made to favor the production of 2-methylene-3-buten-1-ol particularly when relatively substantial amounts of $ZnCl_2$ are employed.

The disclosure, including data, illustrate the value and effectiveness of my invention. The examples, the knowledge and background of the field of invention and general principles of chemistry and other applicable sciences have formed the basis from which the broad descriptions of the invention including the ranges of conditions and generic groups of operating components have been developed, and which have formed the basis for my claims here appended.

I claim:

1. A process for preparing a mixture of conjugated and allenic dienols which comprises the steps of:
  (1) adding (a) a solution of a 1- or 2-halo-1,3-hydrocarbyl diene in a diluent comprising an ether optionally with a hydrocarbon to (b) an ether dispersion of an effective amount and effective ratios of magnesium metal, a metal halide, and a saturated aliphatic halide promoter, under reaction conditions, thereby preparing a Grignard reagent of said 1- or 2-halo-1,3-hydrocarbyl diene,
  (2) contacting said Grignard reagent with an effective amount of a carbonyl compound which is an aldehyde or ketone, under reaction conditions, and
  (3) hydrolyzing the carbonyl-treated Grignard reagent from said step (2), thereby preparing said mixture of dienols, wherein when said ratio of said metal halide:said halo-1,3-hydrocarbyl diene is at least about 0.2:1 said mixture of dienols predominates in said conjugated dienol, and when said ratio of said metal halide:said halo-1,3-hydrocarbyl diene is less than about 0.2:1, said mixture of dienols predominates in said allenic dienol, wherein said ether in said diluent is selected from the group consisting of tetrahydrofuran, 1,4-dioxane, dimethyl ether of ethylene glycol, dimethyl ether of diethylene glycol, diethyl ether of ethylene glycol, diethyl ether of diethylene glycol, alone, or in admixture, and wherein said metal salt is the chloride, bromide, or iodide of zinc, cadmium, mercury, or indium, said saturated aliphatic halide promoter is a saturated aliphatic chloride, bromide, or iodide, and wherein when said aliphatic halide promoter is said chloride, further employing iodine as a copromoter, and optionally otherwise, and wherein said 1-halo or 2-halo-1,3-hydrocarbyl diene is represented by the formula:

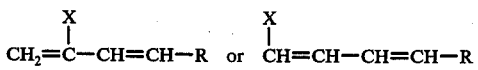

wherein X is chlorine, bromine, iodine, and R is hydrogen or an alkyl radical of 1 to 4 carbon atoms per molecule.

2. The process according to claim 1 employing a ratio of said metal halide:said halo-1,3-hydrocarbyl diene of at least about 0.2:1 whereby in said mixture of said dienols said conjugated dienol predominates.

3. The process according to claim 1 employing a ratio of said metal halide:said halo-1,3-hydrocarbyl diene of less than about 0.2:1 whereby in said mixture of said dienols said allenic dienol predominates.

4. The process according to claim 3 wherein said ratio is in the range of about 0.005:1 to 0.1:1.

5. The process according to claim 1 wherein said metal of said metal salt is said zinc.

6. The process according to claim 1 wherein said metal of said metal salt is said cadmium.

7. The process according to claim 1 wherein said metal of said metal salt is said mercury.

8. The process according to claim 1 wherein said metal of said metal salt is said indium.

9. The process according to claim 1 wherein said saturated aliphatic halide contains 1 to 4 carbon atoms per molecule and 1 to 2 halogen atoms per molecule.

10. The process according to claim 9 wherein said 1- or 2-halo-1,3-diene is 2-bromo-1,3-butadiene, 2-chloro-1,3-butadiene, 2-iodo-1,3-butadiene, 1-bromo-1,3-butadiene, 1-chloro-1,3-butadiene, 1-iodo-1,3-butadiene, 2-chloro-1,3-pentadiene, 2-bromo-1,3-heptadiene, 2-iodo-1,3-octadiene, or a mixture.

11. The process according to claim 9 employing a range of about 0.005:1 to 0.8:1 molar ratio of said metal halide:said 1- or 2-halo-1,3-hydrocarbyl diene, a molar ratio of said saturated aliphatic halide promoter:said metal halide in the range of about 0.02:1 to 50:1, a range of about 0.8 to 1.5 moles of magnesium per mole of said halo-1,3-hydrocarbyl diene, a reaction time of about 0.5 to 24 hours, a reaction temperature in the range of about 10° C. to 100° C., and a pressure sufficient to maintain reactants and diluents substantially in the liquid phase.

12. The process according to claim 11 wherein said halo-1,3-hydrocarbyl diene is a said 2-halo-1,3-hydrocarbyl diene, and wherein said process employs a molar ratio of said metal halide:said 2-halo-1,3-hydrocarbyl diene in the range of about 0.2:1 to 0.8:1 whereby in said mixture of said dienols, said conjugated dienol predominates.

13. The process according to claim 12 wherein said ratio is about 0.5:1.

14. The process according to claim 11 wherein said halo-1,3-hydrocarbyl diene is a said 1-halo-1,3-hydrocarbyl diene, and wherein the molar ratio of said metal halide:said 1-halo-1,3-hydrocarbyl diene is in the range of about 0.2:1 to 0.8:1 whereby in said mixture of said dienols, said conjugated dienol predominates.

15. The process according to claim 11 wherein said molar ratio of said saturated aliphatic halide promoter:-metal halide catalyst is in the range of about 5:1 to 20:1.

16. The process according to claim 11 wherein said ether diluent further comprises a minor amount of benzene, an alkylated derivative thereof, or a saturated aliphatic hydrocarbon.

17. The process according to claim 11 wherein said metal halide is zinc chloride, said ether is tetrahydrofuran, said saturated aliphatic promoter is methyl iodide, and said 1- or 2-halo-1,3-hydrocarbyl diene is 2-chloro-1,3-butadiene, said carbonyl compound is formaldehyde, and the dienol products are the conjugated dienol 2-methylene-3-buten-1-ol and the allenic dienol 3,4-pentadien-1-ol.

18. The process according to claim 11 wherein said metal halide is zinc chloride, said ether is tetrahydrofuran, said saturated aliphatic promoter is methyl iodide, said 1- or 2-halo-1,3-hydrocarbyl diene is 2-chloro-1,3-butadiene, and said carbonyl compound is benzaldehyde, whereby the dienols are 1-phenyl-2-methylene-3-buten-1-ol and 1-phenyl-3,4-pentadien-1-ol.

19. The process according to claim 11 wherein said metal halide is indium chloride, said ether is tetrahydrofuran, said saturated aliphatic promoter is methyl iodide, and said 1- or 2-halo-1,3-hydrocarbyl diene is 2-chloro-1,3-butadiene, said carbonyl compound is formaldehyde, and the dienol products are the conjugated dienol 2-methylene-3-buten-1-ol and the allenic dienol is 3,4-pentadien-1-ol.

20. The process according to claim 11 wherein said metal halide is zinc bromide, said ether is tetrahydrofuran, said saturated aliphatic promoter is methyl iodide, said 1- or 2-halo-1,3-hydrocarbyl diene is 2-chloro-1,3-butadiene, and said carbonyl compound is benzaldehyde, whereby the dienol products are 1-phenyl-2-methylene-3-buten-1-ol and 1-phenyl-3,4-pentadien-1-ol.

21. The process according to claim 11 wherein said metal halide is zinc iodide, said ether is tetrahydrofuran, said saturated aliphatic promoter is methyl iodide, and said 1- or 2-halo-1,3-hydrocarbyl diene is 2-chloro-1,3-butadiene, said carbonyl compound is formaldehyde, and the dienol products are the conjugated dienol 2-methylene-3-buten-1-ol and the allenic dienol is 3,4-pentadien-1-ol.

22. The process according to claim 11 wherein said metal halide is cadmium chloride, said ether is tetrahydrofuran, said saturated aliphatic promoter is methyl iodide, said 1- or 2-halo-1,3-hydrocarbyl diene is 2-chloro-1,3-butadiene, and said carbonyl compound is benzaldehyde, whereby the dienol products are 1-phenyl-2-methylene-3-buten-1-ol and 1-phenyl-3,4-pentadien-1-ol.

23. The process according to claim 11 wherein said metal halide is mercury chloride, said ether is tetrahydrofuran, said saturated aliphatic promoter is methyl iodide, said 1- or 2-halo-1,3-hydrocarbyl diene is 2-chloro-1,3-butadiene, and said carbonyl compound is benzaldehyde, whereby the dienol products are 1-phenyl-2-methylene-3-buten-1-ol and 1-phenyl-3,4-pentadien-1-ol.

24. The process according to claim 1 wherein in said diluent said ether is tetrahydrofuran, the dimethyl or diethyl ether of ethylene glycol, or diethylene glycol.

25. A method for controlling the predominance of conjugated versus allenic dienols in a process of preparing dienols which comprises the steps of:
(a) adding an ethereal solution of a 1- or 2-halo-1,3-hydrocarbyl diene to effective amounts and ratios of an ethereal dispersion of magnesium metal, a metal halide, and a saturated aliphatic halide promoter, under Grignard-forming conditions, employing a ratio of about 0.005:1 to 0.8:1 molar ratio of said metal halide:said 1- or 2-halo-1,3-hydrocarbyl diene, wherein said metal halide is the chloride, bromide, or iodide, of zinc, cadmium, mercury, or indium, said saturated aliphatic halide promoter is a chloride, bromide, or iodide, further with elemental iodine copromoter when said saturated aliphatic halide is the chloride, and optionally otherwise, and said ether is tetrahydrofuran, 1,4-dioxane, dimethyl ether of ethylene glycol, dimethyl ether of diethylene glycol, diethyl ether of ethylene glycol, diethyl ether of diethylene glycol, or mixture, thereby forming a Grignard reagent of said 1-halo- or 2-halo-1,3-hydrocarbyl diene, (b) reacting said Grignard reagent of said 1-halo- or 2-halo-1,3-hydrocarbyl diene with a carbonyl compound which is an aldehyde or ketone in an effective amount, under reaction conditions, and (c) hydrolyzing the reaction mixture from said step (b) under hydrolysis conditions, thereby preparing said dienols comprising a mixture of conjugated and allenic dienols, wherein said conjugated dienol predominates at a ratio of said metal halide:said 1- or 2-halo-1,3-hydrocarbyl diene above about 0.2:1, and wherein said allenic dienol predominates at a ratio of less than about 0.2:1, and wherein said 1-halo or 2-halo-1,3-hydrocarbyl diene is represented by the formula:

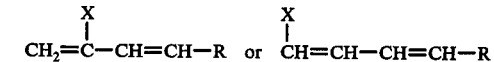

wherein X is chlorine, bromine, or iodine, and R is hydrogen, or an alkyl radical containing 1 to 4 carbon atoms per molecule.

26. The process according to claim 25 wherein said aldehyde or ketone is represented, respectively, by the formulae R"CHO and R'"COR'", wherein said R" is hydrogen, or an alkyl, aryl, cycloalkyl, or combination such that the aldehyde contains 1 to 12 carbon atoms per molecule; R'" is alkyl, cycloalkyl, aryl, or combination hydrocarbon radical, such that said ketone contains 3 to 15 carbon atoms per molecule.

27. The process according to claim 26 wherein said carbonyl compound is said aldehyde, and is selected from the group consisting of formaldehyde, acetaldehyde, propionaldehyde, glyoxal, isobutyraldehyde, paraldehyde, benzaldehyde, n-butyraldehyde, phenyl acetaldehyde, cyclohexyl acetaldehyde, n-decanal, and any of the tolualdehydes.

28. The process according to claim 26 wherein said carbonyl compound is said ketone, and is selected from the group consisting of acetone, ethylmethyl ketone, isopropylmethyl ketone, acetophenone (phenyl methyl ketone), methyl cyclohexyl ketone, benzophenone (diphenyl ketone).

29. The process according to claim 26 wherein said dienols are represented by the formulae:

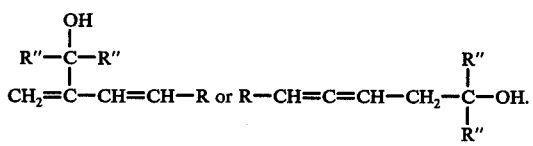

30. The process according to claim 25 wherein said (a) contacting step employs a contacting temperature in the range of about 10° C. to 100° C., a time of about 0.5 to 24 hours, and pressures sufficient to maintain reactants and diluent substantially in the liquid phase; a ratio of said saturated aliphatic halide:said metal halide in the range of about 0.02:1 to 50:1; a molar ratio of said metal halide; said 1- or 2-halo-1,3-diene in the range of about 0.005:1 to 0.8:1; and a ratio of about 0.8 to 1.5 moles of said magnesium per mole of said halo-1,3-diene.

31. The process according to claim 30 wherein said (b) reaction with said carbonyl compound is conducted at a temperature in the range of about −50° C. to +75° C. for a time of about 0.1 to 5 hours, under a pressure sufficient to maintain reactants and diluents substantially in the liquid phase, and employing in a molar ratio of about 0.8:1 to 2.0:1 of said carbonyl compound relative to the amount of said halo-1,3-diene employed.

32. The process according to claim 31 wherein said 1- or 2-halo-1,3-hydrocarbyl diene is 2-bromo-1,3-butadiene, 2-chloro-1,3-butadiene, 2-iodo-1,3-butadiene, 1-bromo-1,3-butadiene, 1-chloro-1,3-butadiene, 1-iodo-1,3-butadiene, 2-chloro-1,3-pentadiene, 2-bromo-1,3-heptadiene, 2-iodo-1,3-octadiene, or a mixture.

33. The process according to claim 32 wherein said metal of said metal salt is said zinc.

34. The process according to claim 31 wherein said hydrolysis is conducted by treating the reaction mixture from said step (b) with water, water and a mineral acid, or water and ammonium chloride, under hydrolysis conditions effective to produce said dienols.

35. The process according to claim 34 wherein said metal halide is zinc chloride, indium chloride, zinc bromide, zinc iodide, or mercury chloride.

36. The process according to claim 35 wherein said metal halide is zinc chloride, said ether diluent is tetrahydrofuran, said saturated aliphatic halide promoter is methyl iodide, said halo-1,3-hydrocarbyl diene is 2-chloro-1,3-butadiene, said carbonyl compound is an aldehyde and is formaldehyde, and the ultimate products obtained comprise 3,4-pentadien-1-ol and 2-methylene-3-buten-1-ol.

37. The process according to claim 31 employing the 2-halo-1,3-hydrocarbyl diene and a mole ratio above about 0.2:1 of said metal halide:said 2-halo-1,3-hydrocarbyl diene, whereby the said conjugated dienol predominates in said dienols product.

38. The process according to claim 31 employing said 2-halo-1,3-hydrocarbyl diene, and a mole ratio of less than about 0.2:1 of said metal halide:said 2-halo-1,3-hydrocarbyl diene, whereby the said allenic product predominates in said dienols product.

* * * * *

UNITED STATES PATENT AND TRADEMARK OFFICE
CERTIFICATE OF CORRECTION

PATENT NO. : 4,087,468

DATED : May 2, 1978

INVENTOR(S) : Paul W. Solomon

It is certified that error appears in the above-identified patent and that said Letters Patent are hereby corrected as shown below:

Column 10, line 14, change "salt" to --- halide ---;

Column 10, line 42, change "salt" to --- halide ---;

Column 10, line 44, change "salt" to --- halide ---;

Column 10, line 46, change "salt" to --- halide ---;

Column 10, line 48, change "salt" to --- halide ---; and

Column 14, line 10, change "salt" to --- halide ---.

Signed and Sealed this

Ninth Day of January 1979

[SEAL]

Attest:

RUTH C. MASON
Attesting Officer

DONALD W. BANNER
Commissioner of Patents and Trademarks